United States Patent [19]

Costales et al.

[11] Patent Number: 4,486,422

[45] Date of Patent: Dec. 4, 1984

[54] INSECTICIDAL PHOSPHORUS DERIVATIVES OF 5-PYRIMIDINOLS

[75] Inventors: Mark J. Costales, Concord; Walter Reifschneider, Walnut Creek; Doris L. Paroonagian, Pleasant Hill, all of Calif.

[73] Assignee: The Dow Chemical Company, Midland, Mich.

[21] Appl. No.: 443,418

[22] Filed: Nov. 22, 1982

[51] Int. Cl.$^3$ .................. C07F 9/65; A01N 57/32
[52] U.S. Cl. .................... 424/200; 544/243; 544/84; 544/122
[58] Field of Search ............ 544/243, 122, 84; 424/200

[56] References Cited

U.S. PATENT DOCUMENTS

| | | | |
|---|---|---|---|
| 3,880,958 | 4/1975 | Hoffmann et al. | 260/944 |
| 3,882,103 | 5/1975 | Beriger et al. | 424/200 X |
| 3,888,951 | 6/1975 | Hoffmann et al. | 260/945 |
| 3,906,094 | 9/1975 | Snell et al. | 424/200 |
| 3,951,975 | 4/1976 | Hofer et al. | 544/243 |
| 3,966,921 | 6/1976 | Beriger et al. | 424/200 X |
| 3,975,522 | 8/1976 | Bader | 424/200 |
| 4,012,506 | 3/1977 | Balke et al. | 424/200 |
| 4,014,882 | 3/1977 | Sharpe | 544/243 |
| 4,127,652 | 11/1978 | Maurer et al. | 424/200 |
| 4,202,889 | 5/1980 | Maurer et al. | 424/200 |
| 4,219,547 | 8/1980 | Gutman | 424/212 |
| 4,254,113 | 3/1981 | Maurer et al. | 424/200 |
| 4,261,983 | 4/1981 | Maurer et al. | 424/200 |
| 4,325,948 | 4/1982 | Maurer et al. | 424/200 |
| 4,326,059 | 4/1982 | Gargano et al. | 544/243 |
| 4,429,125 | 1/1984 | Reifschneider | 424/200 X |
| 4,444,764 | 4/1984 | Reifschneider et al. | 424/200 |

FOREIGN PATENT DOCUMENTS 2055103  2/1981  United Kingdom ............... 424/200

OTHER PUBLICATIONS

Inoue et al., Chemical Abstracts, vol. 57, 824f–826b (1962).

*Primary Examiner*—Donald G. Daus
*Assistant Examiner*—Diana G. Rivers
*Attorney, Agent, or Firm*—S. Preston Jones; Ronald G. Brookens

[57] ABSTRACT

Phosphorus derivatives of 5-pyrimidinols which possess insecticidal properties and especially both systemic and foliar activity for plants against insect pests.

24 Claims, No Drawings

INSECTICIDAL PHOSPHORUS DERIVATIVES OF 5-PYRIMIDINOLS

BACKGROUND OF THE INVENTION

The present invention relates to new phosphorus derivatives of 5-pyrimidinols which possess insecticidal properties and especially both systemic and foliar activity for plants against insect pests. The present invention is also directed to the preparation of said derivatives, active insecticidal compositions containing said derivatives and to the use of such compositions for the kill and control of said pests.

SUMMARY OF THE INVENTION

The present invention is directed to phosphorus derivatives of 5-pyrimidinols which correspond to the formula

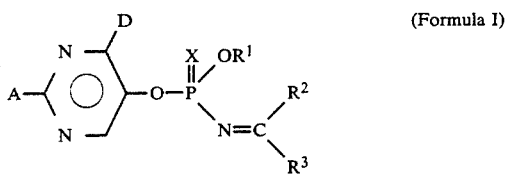

(Formula I)

wherein
A represents hydrogen, alkyl, alkoxy, perfluoroloweralkyl, cycloalkyl, alkyl(cycloalkyl), (cycloalkyl)alkyl, phenyl, alkylthioalkyl, alkoxyalkyl, dialkylaminoalkyl, alkylthio, alkylsulfinyl, alkylsulfonyl, phenylthio, phenylsulfinyl, phenylsulfonyl, (alkylthio)alkylthio, alkoxyalkylthio, dialkylaminoalkylthio, dialkylamino, morpholino, piperidino, N-methylpiperazino, pyrrolidino or ((dimethylamino)methylene)amino (—N=CH—N(CH$_3$)$_2$);
D represents hydrogen or alkyl;
X represents oxygen or sulfur;
R$^1$ represents alkyl;
R$^2$ represents alkyl, alkoxy or dialkylamino; and
R$^3$ represents hydrogen or alkyl.

These above compounds have been found to have good pesticidal properties especially insecticidal, miticidal, acaricidal and nematicidal properties. The compounds also have systemic activity in plants and foliar activity on plants against attack by said pests.

In the present specification and claims, the terms "alkyl", and "alkoxy" as employed in the terms "alkyl", "alkoxy" or as a part of the terms "alkyl(cycloalkyl)", "(cycloalkyl)alkyl", "alkylthio alkyl", "alkoxyalkyl", "dialkylaminoalkyl", "alkylthio", "alkylsulfinyl", "alkylsulfonyl", "(alkylthio)alkylthio", "alkoxyalkylthio", "dialkylaminoalkylthio" and "dialkylamino" designates straight or branched chain alkyl or alkoxy groups of 1 to 6 carbon atoms.

In the present specification and claims, the term "cycloalkyl" as employed in the term "cycloalkyl" or as a part of the terms "alkyl(cycloalkyl)", "(cycloalkyl)alkyl" designates a cycloalkyl group of from 3 to 6 carbon atoms.

The term "perfluoroloweralkyl" designates a perfluoroalkyl group of 1 to 3 carbon atoms.

The compounds of the present invention are largely somewhat viscous oils or solids which are rather readily soluble in many common organic solvents and of low solubility in water.

The compounds of the present invention can be prepared by the reaction of a molar equivalent of an appropriate 5-pyrimidinyl phosphoramidothioate or phosphoramidate corresponding to the formula

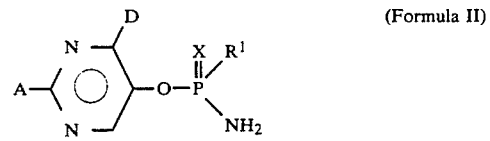

(Formula II)

with from about a 10 to about a 30 percent excess of an appropriate substituted dialkyl acetal corresponding to the formula (R$^4$O)$_2$CR$^2$R$^3$ (Formula III)

wherein A, D, X, R$^1$, R$^2$ and R$^3$ are as hereinabove defined and R$^4$ is alkyl.

In carrying out this reaction, the dialkyl acetal reactant is added to a solution of the phosphoramidothioate (phosphoramidate) reactant in a solvent such as methylene chloride, diethyl ether, toluene or carbon tetrachloride. The mixture is stirred at room temperature for from about 30 minutes to about 4 hours. The solvent is then removed by evaporation. The crude product which remains as a residue is taken up in a solvent such as ether (ethyl ether) and the ether solution washed with water and then a saturated sodium chloride solution. The ether solution is then dried and the ether is removed by evaporation leaving the desired product.

The 5-pyrimidinyl phosphoramidothioate or phosphoramidate employed as a starting material and corresponding to the formula

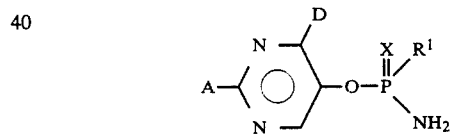

wherein A, D, X and R$^1$ are as hereinabove defined can be prepared by bubbling excess ammonia into a stirring mixture of a 5-pyrimidinyl phosphorochloridothioate or phosphorochloridate reactant in a solvent such as acetonitrile. The reaction is usually carried out at a temperature of from about minus (—) 10° to about 80° C. for a period of from about one to about 16 or more hours. After the completion of the reaction, the reaction mixture is filtered and the residue remaining is purified by high pressure liquid chromatography, if necessary.

The 5-pyrimidinyl phosphorochloridothioate or phosphorochloridate employed as a starting material can be prepared by reacting substantially equimolar amounts of an appropriate 5-pyrimidinol reactant corresponding to the formula

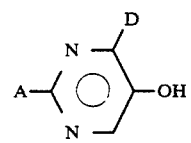

wherein A and D are as hereinbefore defined, and an appropriate phosphorodichloridate or phosphorodichloridothioate corresponding to the formula

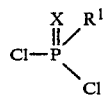

wherein $R^1$ is as hereinbefore defined in the presence of a solvent and a hydrogen chloride absorber.

In carrying out the reaction, the reactants are mixed in any suitable fashion and maintained together with agitation until the reaction is complete. It is convenient to first mix the pyrimidinol with the solvent and the HCl acceptor and then add the phosphorus reactant. The reaction is complete when all of the phosphorus reactant has been consumed.

Representative solvents include, for example, acetonitrile, cyclohexane, benzene, toluene, xylene, acetone, methylene chloride, methylethyl ketone, diethylether, dioxane, tetrahydrofuran and the like.

Representative hydrogen chloride absorbers (acid-binding agents) include, for example, alkali metal carbonates such as sodium and potassium carbonates and tertiary amines such as, for example, trimethylamine, triethylamine, pyridine and the like.

At the completion of the reaction, the reaction mixture is filtered to remove any insolubles and the filtrate concentrated under reduced pressure. The residue is then taken up in ethyl ether, benzene, toluene, methylene chloride or chloroform and washed thoroughly with water and then with a saturated sodium chloride solution and dried. The solvent is removed by evaporation under reduced pressure leaving the desired product.

While the above discussion is directed to the preparation and recovery of each of the intermediates, the present compounds can also be prepared in situ with no separation of the intermediates.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

N-((Dimethylamino)methylene) O-ethyl O-(2-(1-methylethyl)-5-pyrimidinyl) phosphoramidothioate

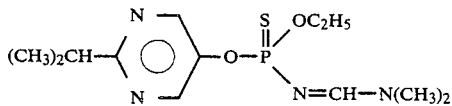

To a solution of 3.2 grams (g) (0.012 mole (m)) of O-ethyl O-(2-(1-methylethyl)-5-pyrimidinyl) phosphoramidothioate in 100 milliliters (ml) of methylene chloride was added 1.77 g (0.015 m) of dimethylformamide dimethyl acetal. The mixture was stirred for one hour at room temperature and the solvent was then removed in a rotary evaporator. The oil which remained as a residue was dissolved in ethyl ether and the ether solution washed with water then with a saturated sodium chloride solution and then dried over anhydrous sodium sulfate. The ether was removed in a rotary evaporator leaving 2.7 g of the above-named product as an amber colored oil. The product had a refractive index of n(25/d)=1.5379. The IR and NMR spectra were in agreement with the desired structure. Upon analysis, the product was found to have carbon, hydrogen and nitrogen contents of 45.89, 6.83 and 17.34 percent, respectively, as compared with the theoretical contents of 45.55, 6.69 and 17.71 percent, respectively, as calculated for the above-named structure.

EXAMPLE II

N-((Dimethylamino)methylene) O-ethyl O-(2-cyclopropyl-5-pyrimidinyl) phosphoramidothioate

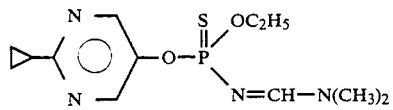

To a stirred mixture of 2.3 g (0.017 m) of 2-cyclopropyl-5-pyrimidinol, 3.0 g of finely powdered potassium carbonate and 100 ml of acetonitrile was added 3.02 g (0.017 m) of O-ethyl phosphorodichloridothioate. The mixture was stirred at room temperature until no more of the phosphorus reactant could be detected by gas-liquid chromatography (glc). An excess of ammonia was then bubbled into the reaction mixture and stirring at room temperature was continued for about one hour. The mixture was filtered to remove the insoluble salts and the salts were washed with acetonitrile and the acetonitrile added to the filtrate. The filtrate was concentrated under reduced pressure to an amount of about 50 ml. To this solution, 2.1 g (0.018 m) of dimethylformamide dimethyl acetal was added and the mixture was stirred at room temperature for 16 hours. The reaction mixture was concentrated in a rotary evaporator, the residual oil was taken up in ether, washed twice with 5% aqueous sodium hydroxide, once with a saturated sodium chloride solution and dried over anhydrous sodium sulfate. The solvent was removed in a rotary evaporator leaving 0.7 g of the desired product, as named above, as an amber colored oil. The product had a refractive index of n(25/d)=1.5553 and the IR and NMR spectra confirmed the structure. Upon analysis, the compound was found to have carbon, hydrogen and nitrogen contents of 45.87, 5.69 and 17.56 percent, respectively, as compared with the theoretical contents of 46.00, 5.79 and 17.88 percent, respectively, as calculated for the above-named structure.

EXAMPLE III

N-((Dimethylamino)methylene) O-ethyl O-(2-(1,1-dimethylethyl)-5-pyrimidinyl) phosphoramidothioate

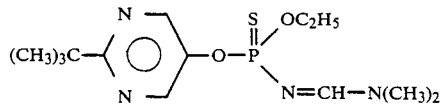

To a stirred mixture of 5.5 g (0.036 m) of 2-(1,1-dimethylethyl)-5-pyrimidinol, 5.5 g of finely powdered potassium carbonate and 100 ml of acetonitrile was added 6.47 g (0.036 m) of O-ethyl phosphorodichloridothioate. The mixture was stirred at room temperature until no more of the phosphorus reactant could be detected by glc. A small excess of ammonia was then bubbled into the reaction mixture and stirring at room temperature was continued until all of the starting materials were converted to the amidothiophosphate. The salts were then removed by filtration and the filtrate concentrated under vacuum to ~50 ml. To this solution was added 5.32 g of dimethylformamide dimethyl acetal and stirring at room temperature continued until no more starting material could be detected by glc. The mixture was concentrated under reduced pressure, and the residual oil taken up in ether. The ether solution was washed twice with 5% aqueous sodium hydroxide, once with a saturated sodium chloride solution and dried over anhydrous sodium sulfate. The solvent was removed in a rotary evaporator leaving 0.8 g of the above-indicated compound as an amber colored oil. The product had a refractive index of n(25/d)=1.5216 and the IR and NMR spectra confirmed the structure of the above-indicated compound. Upon analysis, the compound was found to have carbon, hydrogen and nitrogen contents of 47.46, 6.97, and 16.39, respectively, as compared with the theoretical contents of 47.25, 7.01 and 16.95 percent, respectively, as calculated for the above-named compound.

EXAMPLE IV

O-Ethyl O-(2-(1-methylethyl)-5-pyrimidinyl)phosphoramidothioate

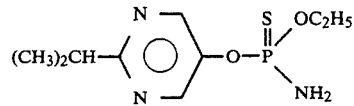

To a stirred mixture of 12.0 g (0.087 m) of 2-(1-methylethyl)-5-pyrimidinol, 12.0 g of finely powdered potassium carbonate and 100 ml of acetonitrile was added 15.5 g (0.087 m) of O-ethyl phosphorodichloridothioate. The mixture was stirred at room temperature overnight. Excess ammonia was bubbled into the reaction mixture at 0° C. and the mixture was stirred overnight. The salts which formed were removed by filtration and the residual oil purified by high pressure liquid chromatography. The above-indicated compound was recovered as a pale amber oil in a yield of 13.4 g (60% of theoretical). The product had a refractive index of n(25/d)=1.5285 and the IR and NMR spectra confirmed the structure of the indicated compound. Upon analysis, the compound was found to have carbon, hydrogen and nitrogen contents of 41.64, 6.22 and 16.89 percent, respectively, as compared with the theoretical contents of 41.36, 6.17 and 16.08 percent respectively, as calculated for the above-named compound.

By following the preparative procedures as outlined in the above methods of preparation and the above examples and employing the appropriate starting materials, the following compounds set forth in Table 1 are prepared.

TABLE 1

| A | D | X | R¹ | R² | R³ |
|---|---|---|---|---|---|
| —H | —H | S | —OCH₃ | —N(CH₃)₂ | —H |
| —H | —H | O | —OC₂H₅ | —N(CH₃)₂ | —H |
| —CH₃ | —CH₃ | S | —OC₂H₅ | —N(CH₃)₂ | —CH₃ |
| —C₆H₁₃ | —C₆H₁₃ | O | —OC₆H₁₃ | —N(C₆H₁₃)₂ | —H |
| —OCH₃ | —C₆H₁₃ | O | —OCH₃ | —OCH₃ | —CH₃ |
| —OC₆H₁₃ | —H | O | —OC₂H₅ | —C₃H₇ | —H |
| —CF₃ | —H | S | —OC₄H₉ | —OC₂H₅ | —H |
| —C₃F₇ | —C₃H₇ | S | —OC₆H₁₃ | —N(C₂H₅)₂ | —H |
| —◁ | —H | S | —OC₂H₅ | —N(C₃H₇)₂ | —H |
| —C₆H₁₁— (cyclic) | —H | S | —OC₂H₅ | —OCH₃ | —C₆H₁₃ |
| —ø | —H | S | —OC₂H₅ | —OC₆H₁₃ | —H |
| —CH₂SCH₃ | —H | S | —OC₂H₅ | —N(C₂H₅)₂ | —H |
| —CH₂—◁ | —H | S | —OC₅H₁₁ | —CH₃ | —H |
| ◁—CH₃ | —H | O | —OC₂H₅ | —N(CH₃)₂ | —H |
| —C₂H₄OC₆H₁₃ | —CH₃ | O | —OC₃H₇ | —OC₂H₅ | —CH₃ |
| —CH₂—N(CH₃)₃ | —CH₃ | S | —OCH₃ | —OC₂H₅ | —C₂H₅ |
| —SCH₃ | —C₄H₉ | S | —OC₂H₅ | —OC₂H₅ | —H |

TABLE 1-continued

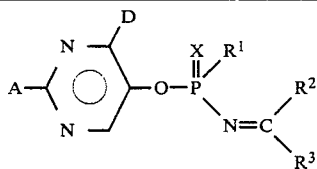

| A | D | X | R¹ | R² | R³ |
|---|---|---|----|----|----|
| $-SOC_4H_9$ | $-H$ | S | $-OCH_3$ | $-OCH_3$ | $-CH_3$ |
| $-SO_2C_2H_5$ | $-H$ | S | $-OC_2H_5$ | $-OC_2H_5$ | $-H$ |
| $-S-\emptyset$ | $-C_2H_5$ | S | $-OC_2H_5$ | $-C_4H_9$ | $-C_4H_9$ |
| $-SO-\emptyset$ | $-C_5H_{11}$ | S | $-OCH_3$ | $-OC_4H_9$ | $-H$ |
| $-SO_2-\emptyset$ | $-H$ | S | $-OC_3H_7$ | $-N(C_4H_9)_2$ | $-H$ |
| $-SCH_2SC_4H_9$ | $-H$ | S | $-OC_2H_5$ | $-N(CH_3)_2$ | $-CH_3$ |
| $-SC_2H_4OC_6H_{13}$ | $-H$ | O | $-OC_2H_5$ | $-N(CH_3)_2$ | $-CH_3$ |
| $-SC_2H_4N(CH_3)_3$ | $-H$ | O | $-OC_2H_5$ | $-CH_3$ | $-CH_3$ |
| $-N(C_6H_{13})_2$ | $-H$ | O | $-OC_2H_5$ | $-CH_3$ | $-H$ |
| $-N=CH-N(CH_3)_2$ | $-H$ | S | $-OC_2H_5$ | $-N(CH_3)_2$ | $-H$ |
| 3-Morpholino | $-H$ | S | $-OCH_3$ | $-N(C_2H_5)_2$ | $-C_2H_5$ |
| 3-Piperidino | $-H$ | S | $-OC_2H_5$ | $-N(CH_3)_2$ | $-H$ |
| 4-N—methyl piperazino | $-H$ | S | $-OC_3H_7$ | $-CH_3$ | $-H$ |
| 3-Pyrrolidino | $-H$ | O | $-OC_2H_5$ | $-N(C_4H_9)_2$ | $-H$ |
| ◁ | $-CH_3$ | S | $-OC_2H_5$ | $-N(CH_3)_2$ | $-H$ |

The compounds of the present invention are very effective for the kill and control of insects found on the roots or aerial portions of growing plants.

Representative of the various insects which are killed and controlled by the active compounds of the present invention include the mites (Acarina) in particular, the spider mites (Tetranychidae) such as the two-spotted spider mite (Tetranychus urticae), carmine spider mite (Tetranychus cinnabarinus) and the European red mite (Panonychus ulmi), blister mites, for example, the currant blister mite (Eriophyes ribis) and tarsonemids, for example, the broad mite (Hemitarsonemus latus), the cyclamen mite (Tarsonemus pallidus); leafhoppers and planthoppers, i.e., aster leafhopper (Macrosteles fascifrons), rice green leafhopper (Nephotettix virescens), zig-zag leafhopper (Recilia dorsalis), (Nephotettix apicalis), white-back planthopper (Sogattella furcifera), brown planthopper (Nilaparvata lugens), smaller brown planthopper (Laodelphax striatellus), grape leafhopper (Erythroneura sp) and potato leafhopper (Empoasca fabae); for insects such as aphids (Aphididae) such as the green peach aphid (Myzus persicae), the bean aphid (Aphis fabae), the black cherry aphid (Myzus ceraci), the pea aphid (Acythorsiphum pisum) and the potato aphid (Macrosiphum euphorbiae), the currant gall aphid (Cryptomyzus ribis), the mealy apple aphid (Sappaphis mali), the mealy plum aphid (Hyalopterus pruni), the cotton aphid (Aphis gossyppii); and other such insects including tobacco budworms (Heliothis virescens), Western spotted cucumber beetle (Diabrotica undecimpunctata undecipunctata), the rice water weevil (Lissorhoptrus orvsophilus), housefly (Musca domestica), beet armyworm (Spodoptora exigua), and codling moth (Laspeyresia pomonella); and borers such as rice stem borer (Chilo sp), the pink borer (Sesamia sp) and the paddy borer (Tryporyza sp).

In the present specification and claims, the term "systemic" defines the translocation of the active compound employed in the present method through the plant. The active compound can be applied either to the above-ground or preferably to below-ground portions of the plant.

The application of an insecticidally effective amount of an active compound of the present invention is critical to the method of the present invention. The active compound can sometimes be employed in unmodified form. Frequently, however, for easier application, the compound is modified by the employment with it of an adjuvant or inert carrier therefor. Therefore, the practical employment of the beneficial utilities of the present compound often requires that the compound be composited with one or more adjuvant substances which are chemically inert to the active compound, and the resulting compositions are comprehended within the present invention.

The compositions can be formulated in various forms, such as emulsifiable concentrates, wettable powders, flowable suspension dusts, granules, microencapsulated granules, fine granules, oil sprays, aerosols, and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the active compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become available to those skilled in the art in view of the teachings set forth hereinbelow.

The exact concentration of the active compound in a composition thereof with an adjuvant therefor can vary; it is only necessary that the active compounds be present in a sufficient amount so as to make possible the application of an insecticidally effective dosage. Generally, for practical applications, the active compounds can be broadly applied to the plants or to the soil around the roots of the plants or to water, such as in broadcast rice paddy applications in compositions containing from about 0.00001 percent to about 98 percent by weight of the active compound.

In preparation of dust compositions, the product can be compounded with any of the finely divided carrier solids such as prophyllite, diatomaceous earth, gypsum and the like. In such operations, the finely divided carrier is ground or mixed with the active compound, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, the active compound or a dust concentrate composition containing said compound can be incorporated in intimate mixture with surface-active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the active compound can be compounded with a suitable water-immiscible organic liquid and a surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene liquid halohydrocarbons and synthetic organic oils. The surface-active dispersing agents are usually employed in liquid compositions in the amount of from 0.1 to 20 percent by weight of the combined weight of the dispersing agent and active compound.

When operating in accordance with the present invention, the active compound or a composition containing the active compound is applied to the plants or to their habitat in any convenient manner, for example, by means of hand dusters or sprayers. Application to the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane.

In further embodiments, one of the compounds of the present invention or compositions containing the same, can be advantageously employed in combination with one or more additional pesticidal compounds. Such additional pesticidal compounds may be insecticides, nematocides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use, or as an additament. The compounds in combination can generally be present in the ratio of from about 1 to about 99 parts of the compound of the present invention with from about 99 to about 1 part of the additional compound(s).

Dosage amounts are generally from 15–1,000 grams (g) preferably from 40–600 g of active compound and most preferably from 125–500 g of active compound per hectare. However, in special cases, it is possible to exceed or reduce the amount and this may sometimes be necessary.

EXAMPLE V

Aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole toxicant. Separate cotton plants were infested with ~50–100 two-spotted spider mites and the plants injected at the base of the plants with one of the dispersions. In a like manner, ~50–100 two-spotted spider mites were placed on control plants and the plants also injected at the base with a solution containing only water and surfactant. The plants were maintained under conditions conducive to the growth of the plants and the mites. After a period of 5 days, the plants were examined to determine the percent kill and control by the active compound. It was found that at a dosage rate of 25 parts of the active compound per million parts of the ultimate dispersion (ppm) each of the compounds N-((dimethylamino)methylene) O-ethyl O-(2-(1-methylethyl)-5-pyrimidinyl) phosphoramidothioate, N-((dimethylamino)methylene) O-ethyl O-(2-cyclopropyl-5-pyrimidinyl) phosphoramidothioate and N-((dimethylamino)methylene) O-ethyl O-(2-(1,1-dimethylethyl)-5-pyrimidinyl) phosphoramidothioate gave 100 percent kill and control of the two-spotted spider mites.

EXAMPLE VI

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant.

Separate rice plants were dipped into each of the dispersions and permitted to dry.

A plastic cylinder was placed around each of the plants and 10 adult aster leafhoppers were placed into the cylinder and the cylinder capped. In a like manner, 10 adult aster leafhoppers were placed on control plants which had been dipped in a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 25 parts of the active compound per million parts of the ultimate dispersion (ppm) each of the compounds N-((dimethylamino)methylene) O-ethyl O-(2-(1-methylethyl)-5-pyrimidinyl) phosphoramidothioate, N-((dimethylamino)methylene) O-ethyl O-(2-cyclopropyl-5-pyrimidinyl) phosphoramidothioate N-((dimethylamino)methylene) O-ethyl O-(2-cyclopropyl-4-methyl-5-pyrimidinyl) phosphoroamidothioate and N-((dimethylamino)methylene) O-ethyl O-(2-(1,1-dimethylethyl)-5-pyrimidinyl) phosphoramidothioate gave 100 percent kill and control of aster leafhoppers.

EXAMPLE VII

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant.

Separate rice plants were treated by adding a predetermined amount of one of the test dispersions to the root of the plant to determine systemic activity.

A plastic cylinder was placed around each of the plants and 10 adult aster leafhoppers were placed into the cylinder and the cylinder capped. In a like manner, 10 adult aster leafhoppers were placed on control plants which were treated at the root zone with a solution containing only water and surfactant. The plants were maintained under conditions conducive to the growth of the plants and leafhoppers. After a period of three days, the cylinder and plants were examined to determine the concentration in parts of the active compound per million parts of the ultimate dispersion necessary to give 100 percent kill and control of the aster leafhopper. It was found that at a dosage rate of 6.25 parts of the active compound per million parts of the ultimate dispersion (ppm) each of the compounds N-((dimethylamino)methylene) O-ethyl O-(2-(1-methylethyl)-5-pyrimidinyl) phosphoramidothioate, N-((dimethylamino)methylene) O-ethyl O-(2-cyclopropyl-5-pyrimidinyl) phosphoramidothioate, N-((dimethylamino)methylene) O-ethyl O-(2-cyclopropyl-4-methyl-5-pyrimidinyl) phosphoramidothioate and N-((dimethylamino)methylene) O-ethyl O-(2-(1,1-dimethylethyl)-5-pyrimidinyl) phosphoramidothioate gave 100 percent kill and control of the aster leafhopper.

EXAMPLE VIII

In this operation, aqueous dispersions were prepared by admixing one of the hereinafter set forth compounds, dissolved in a suitable inert solvent, with a predetermined quantity of water and a predetermined amount of a surfactant to give aqueous dispersions of varying predetermined amounts of one of the compounds as the sole active toxicant. Separate 3 inch discs cut from cotton plant leaves were thoroughly wetted by briefly dipping into one of the dispersions and the wetted leaves were placed in an open petri dish and permitted to dry. After the leaves were dry, 5 live 2nd instar tobacco budworm larvae were placed in each petri dish. In identical operations, 5 like live tobacco budworm larvae were placed in control petri dishes, the leaf therein having been wetted with a solution containing only water and surfactant. The dishes were maintained at about 80° F. under moist conditions conducive for the growth of the tobacco budworm larvae for a period of about 2 days. At the end of the 2-day period, the dishes were examined to determine the minimum concentration in parts of the active compound per million parts of the ultimate dispersion necessary to give at least a 100 percent kill and control of the tobacco budworm larvae. It was found that at a dosage rate of 600 parts of the active compound per million parts of the ultimate dispersion (ppm) each of the compounds N-((dimethylamino)methylene) O-ethyl O-(2-(1-methylethyl)-5-pyrimidinyl) phosphoramidothioate, N-((dimethylamino)methylene) O-ethyl O-(2-cyclopropyl-5-pyrimidinyl) phosphoramidothioate and N-((dimethylamino)methylene) O-ethyl O-(2-(1,1-dimethylethyl)-5-pyrimidinyl) phosphoramidothioate gave 100 percent kill and control of tobacco budworm larvae.

EXAMPLE IX

Seventy-five grams of air-dried soil were placed in an 8-ounce container. To the soil was added sufficient volume of a 400 ppm dispersion, prepared by admixing a predetermined amount of N-((dimethylamino)methylene O-ethyl O-(2-cyclopropyl-5-pyrimidinyl) phosphoramidothioate, dissolved in a suitable inert solvent, with a predetermined amount of water and a predetermined amount of surfactant, to give various predetermined concentrations of the toxicant in the soil on a soil-chemical basis. The treated soil was air-dried and thoroughly mixed. To each treated container, and control containers treated with water and surfactant alone, was added 0.5 milliliters of an aqueous suspension of the eggs of the Western spotted cucumber beetle (WSCB) (70–80 eggs of 3–4 days old). Additional treated soil was used to cover the eggs and a corn seed was placed in the soil and covered with additional treated soil. The containers were thereafter maintained under conditions conducive to the growth of the seeds and the hatching of the eggs. Ten to twelve (10–12) days after treatment, the containers and the plants therein were examined and it was found that the above-indicated compound gave a 100 percent kill and control of the larvae from the hatched eggs at a dosage of 25 ppm in the soil.

EXAMPLE X

In this operation, aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole active toxicant. Separate cotton plant leaves were thoroughly wetted by briefly dipping into one of the dispersions and the wetted leaves placed in an open petri dish and permitted to dry. After the leaves were dry, 5 live beet armyworm larvae, approximately late 2nd instar were placed in each petri dish. In identical operations, 5 live late 2nd instar beet armyworm larvae were placed in control petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the concentration in parts of the active compound per million parts of the ultimate dispersion necessary to give at least a 100 percent kill and control of the beet armyworm larvae. It was found that at a dosage rate of 600 parts of the active compound per million parts of the ultimate dispersion (ppm) each of the compounds N-((dimethylamino)methylene) O-ethyl O-(2-(1-methylethyl)-5-pyrimidinyl) phosphoramidothioate, N-((dimethylamino)methylene) O-ethyl O-(2-cyclopropyl-5-pyrimidinyl) phosphoramidothioate and N-((dimethylamino)methylene) O-ethyl O-(2-(1,1-dimethylethyl)-5-pyrimidinyl) phosphoramidothioate gave 100 percent kill and control of beet armyworm larvae.

EXAMPLE XI

Aqueous dispersions were prepared by admixing one of the hereinafter set forth compounds, dissolved in a suitable inert solvent, with a predetermined quantity of water and a predetermined amount of surfactant to give aqueous dispersions containing varying predetermined amounts of one of the compounds as the sole toxicant.

Small plastic pots were filled to ¼ inch of the top with root-knot nematode infested soil. A predetermined amount of the test dispersion was poured onto the surface of the soil in each pot. In a like manner, a solution of only inert solvent, surfactant and water was poured onto the surface of the soil in each pot serving as a check. The pots were seeded to a host plant and mulch was added to fill the containers to the top. After 3 to 5 weeks of growth in the greenhouse, percent control was determined by comparing the infestation of the treated plants with the untreated checks. It was found that a dosage rate of 0.62 parts per million (ppm) of the active compound in the soil each of the compounds N-((dimethylamino)methylene O-ethyl O-(2-(1-methylethyl)-5-pyrimidinyl) phosphoramidothioate and N-((dimethylamino)methylene) O-ethyl O-(2-(1,1-dimethylethyl)-5-pyrimidinyl) phosphoramidothioate gave 100 percent control of root-knot nematodes.

The pyrimidinols employed as intermediates in the preparation of the present compounds are for the most part known compounds and all can be prepared according to methods described in the literature.

The 2-alkyl-4-methyl-5-pyrimidinols can be prepared by reacting methyl methoxyacetate with sodium hydride in toluene and the product is then reacted with the requisite amidine to give 2-alkyl-5-methoxy-6-methoxymethyl-4-pyrimidinol. This latter compound is chlorinated in the 4-position by reaction with phosphorus oxychlorides. The ring chlorine and the methoxy group in the methylmethoxy group are replaced with hydrogen on reduction with zinc in 1 normal NaOH and reaction with sodium ethyl mercaptide in dimethylformamide then yields the desired pyrimidinol.

In a preferred method of preparation of 2-alkyl-5-pyrimidinols or 2-alkylthio-5-pyrimidinols, phosgene is bubbled into dimethylformamide in methylene chloride medium forming a Vilsmeier reagent which is then allowed to react with methoxyacetaldehyde. The appropriate amidine is then added to the reaction mixture followed by sodium methoxide in methanol. The methylene chloride is distilled or flashed off and the mixture heated under reflux to form the desired 2-alkyl-5-methoxypyrimidine. The methoxy group is converted to the OH group using sodium ethyl mercaptide in dimethylformamide.

In another preferred method of preparation of 5-pyrimidinols, N-(3-(dimethylamino)-2-(phenylmethoxy)-2-propenylidene)-N-methylmethanaminium perchlorate (A. Holy and Z. Arnold, Collect. Czech. Chem. Commun. 38, 1371–80 (1973)) is condensed with the requisite amidine, guanidine, isothiourea or isourea to give the corresponding 2-substituted-5-(phenylmethoxy)pyrimidine. The phenylmethoxy group is converted to the OH group either by catalytic hydrogenation, or by hydrolysis with hydrochloric acid.

The alkylsulfinyl-, phenylsulfinyl-, alkylsulfonyl- and phenylsulfonyl-5-pyrimidinols are prepared by the oxidation of the appropriate alkylthio- or phenylthio-5-pyrimidinol with hydrogen peroxide.

What is claimed is:

1. A compound corresponding to the formula

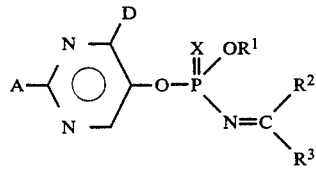

wherein

A represents hydrogen, alkyl, alkoxy, perfluoroloweralkyl, cycloalkyl, alkyl(cycloalkyl), (cycloalkyl)alkyl, phenyl, alkylthioalkyl, alkoxyalkyl, dialkylaminoalkyl, alkylthio, alkylsulfinyl, alkylsulfonyl, phenylthio, phenylsulfinyl, phenylsulfonyl, (alkylthio)alkylthio, alkoxyalkylthio, dialkylaminoalkylthio, dialkylamino, morpholino, piperidino, N-methylpiperazino, pyrrolidino or ((dimethylamino)methylene)amino (—N=CH—N(CH$_3$)$_2$);

D represents hydrogen or alkyl;

X represents oxygen or sulfur;

R$^1$ represents alkyl;

R$^2$ represents alkyl, alkoxy or dialkylamino; and

R$^3$ represents hydrogen or alkyl.

2. A compound as defined in claim 1 wherein A is alkyl.

3. A compound as defined in claim 1 wherein A is cycloalkyl.

4. A compound as defined in claim 3 wherein D is alkyl.

5. The compound as defined in claim 2 which is N-((dimethylamino)methylene) O-ethyl O-(2-(1-methylethyl)-5-pyrimidinyl) phosphoramidothioate.

6. The compound as defined in claim 2 which is N-((dimethylamino)methylene) O-ethyl O-(2-(1,1-dimethylethyl)-5-pyrimidinyl) phosphoramidothioate.

7. The compound as defined in claim 3 which is N-((dimethylamino)methylene) O-ethyl O-(2-cyclopropyl-5-pyrimidinyl) phosphoramidothioate.

8. The compound as defined in claim 4 which is (N-((dimethylamino)methylene) O-ethyl O-(2-cyclopropyl-4-methyl-5-pyrimidinyl) phosphoramidothioate.

9. An insecticidal composition comprising an inert carrier in intimate admixture with an insecticidally effective amount of an active compound corresponding to the formula

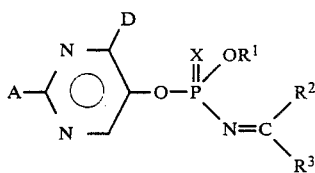

wherein
- A represents hydrogen, alkyl, alkoxy, perfluoroloweralkyl, cycloalkyl, alkyl(cycloalkyl), (cycloalkyl)alkyl, phenyl, alkylthioalkyl, alkoxyalkyl, dialkylaminoalkyl, alkylthio, alkylsulfinyl, alkylsulfonyl, phenylthio, phenylsulfinyl, phenylsulfonyl, (alkylthio)alkylthio, alkoxyalkylthio, dialkylaminoalkylthio, dialkylamino, morpholino, piperidino, N-methylpiperazino, pyrrolidino or ((dimethylamino)methylene)amino (—N=CH—N(CH$_3$)$_2$);
- D represents hydrogen or alkyl;
- X represents oxygen or sulfur;
- R$^1$ represents alkyl;
- R$^2$ represents alkyl, alkoxy or dialkylamino; and
- R$^3$ represents hydrogen or alkyl.

10. A composition as defined in claim 9 wherein A is alkyl.

11. A composition as defined in claim 9 wherein A is cycloalkyl.

12. A composition as defined in claim 11 wherein D is alkyl.

13. The composition as defined in claim 11 wherein the active compound is N-((dimethylamino)methylene) O-ethyl O-(2-(1-methylethyl)-5-pyrimidinyl) phosphoramidothioate.

14. The composition as defined in claim 10 wherein the active compound is N-((dimethylamino)methylene) O-ethyl O-(2-(1,1-dimethylethyl)-5-pyrimidinyl) phosphoramidothioate.

15. The composition as defined in claim 11 wherein the active compound is N-((dimethylamino)methylene) O-ethyl O-(2-cyclopropyl-5-pyrimidinyl) phosphoramidothioate.

16. The composition as defined in claim 12 wherein the active compound is (N-((dimethylamino)methylene) O-ethyl O-(2-cyclopropyl-4-methyl-5-pyrimidinyl) phosphoramidothioate.

17. A method for the kill and control of insects which comprises contacting said insects or their habitat with a composition comprising an inert carrier in intimate admixture with an insecticidally effective amount of an active compound corresponding to the formula

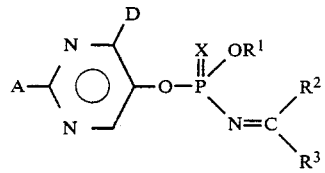

wherein
- A represents hydrogen, alkyl, alkoxy, perfluoroloweralkyl, cycloalkyl, alkyl(cycloalkyl), (cycloalkyl)alkyl, phenyl, alkylthioalkyl, alkoxyalkyl, dialkylaminoalkyl, alkylthio, alkylsulfinyl, alkylsulfonyl, phenylthio, phenylsulfinyl, phenylsulfonyl, (alkylthio)alkylthio, alkoxyalkylthio, dialkylaminoalkylthio, dialkylamino, morpholino, piperidino, N-methylpiperazino, pyrrolidino or ((dimethylamino)methlene)amino (—N=CH—N(CH$_3$)$_2$);
- D represents hydrogen or alkyl;
- X represents oxygen or sulfur;
- R$^1$ represents alkyl;
- R$^2$ represents alkyl, alkoxy or dialkylamino; and
- R$^3$ represents hydrogen or alkyl.

18. A method as defined in claim 17 wherein A is alkyl.

19. A method as defined in claim 17 wherein A is cycloalkyl.

20. A method as defined in claim 19 wherein D is alkyl.

21. The method as defined in claim 18 wherein the active compound is N-((dimethylamino)methylene) O-ethyl O-(2-(1-methylethyl)-5-pyrimidinyl) phosphoramidothioate.

22. The method as defined in claim 18 wherein the active compound is N-((dimethylamino)methylene) O-ethyl O-(2-(1,1-dimethylethyl)-5-pyrimidinyl) phosphoramidothioate.

23. The method as defined in claim 19 wherein the active compound is N-((dimethylamino)methylene) O-ethyl O-(2-cyclopropyl-5-pyrimidinyl) phosphoramidothioate.

24. The method as defined in claim 20 wherein the active compound is (N-((dimethylamino)methylene) O-ethyl O-(2-cyclopropyl-4-methyl-5-pyrimidinyl) phosphoramidothioate.

* * * * *